United States Patent [19]

Thompson

[11] Patent Number: 5,053,629

[45] Date of Patent: Oct. 1, 1991

[54] MICRODENSITOMETER WITH SUBMICRON RESOLUTION HAVING DUAL DIAPHRAGMS AND DUAL MICROSCOPES

[75] Inventor: James S. Thompson, Los Angeles, Calif.

[73] Assignee: The Aerospace Corporation, El Segundo, Calif.

[21] Appl. No.: 572,200

[22] Filed: Aug. 23, 1990

[51] Int. Cl.⁵ .............................................. G01V 9/04
[52] U.S. Cl. ................................ 250/571; 250/237 R; 359/385; 359/368
[58] Field of Search .................. 250/571, 237 R, 216; 350/410, 449, 450, 523; 356/429

[56] References Cited

U.S. PATENT DOCUMENTS

| 2,612,608 | 9/1952 | Miller | 250/237 R |
| 3,876,289 | 4/1975 | DeVeer et al. | 350/523 |
| 4,063,797 | 12/1977 | Taira | 350/523 |
| 4,657,198 | 4/1987 | Shimizu et al. | 250/571 |

Primary Examiner—David C. Nelms
Assistant Examiner—Que T. Le
Attorney, Agent, or Firm—William J. Burke

[57] ABSTRACT

A microdensitometer capable of submicron resolution is achieved by incorporation of adjustable diaphragms situated outside the optics of the microdensitometer.

1 Claim, 3 Drawing Sheets

MICRODENSITOMETER WITH SUBMICRON RESOLUTION HAVING DUAL DIAPHRAGMS AND DUAL MICROSCOPES

STATEMENT OF GOVERNMENT INTEREST

The invention described herein may be manufactured and used by or for the Government of the United States for governmental purposes without the payment of royalty therefor.

BACKGROUND OF THE INVENTION

1. Field of the Invention

This invention relates to microdensitometers, and more particularly to densitometers which are capable of submicron resolution.

2. Description of the Prior Art

An optical microdensitometer is an instrument which scans two dimensional arrays of information and provides information about the transmission at each point in the array. A film sample is an example of an array of information which is scanned by a microdensitometer.

An optical microdensitometer in its classical configuration consists of two microscopes facing each other and separated by that distance which will cause a transparent object placed between them to be in focus simultaneously in both of them. If the numerical apertures of the two microscopes are equal, the image formed by the second microscope will be found to be bordered by bright and dark bands of light that follow the contour of the object being viewed. This phenomenon is referred to as "ringing." Ringing results from the presence of increasing amounts of coherence in the light passing through the optics of the densitometer. Coherence increases as the numerical apertures of the microscopes decrease. This phenomenon degrades the performance of the system.

The standard solution to this problem is to mismatch the numerical apertures of the objective lenses in the two microscopes. Also, the second (output) microscope can be adjusted to examine a slightly smaller area than the area being illuminated by the first (input) microscope.

However, locating objective lenses with different numerical apertures becomes very difficult when the numerical apertures are rather large (e.g. on the order of 0.5 or larger). The fact is that the numerical aperture for a given power objective for high quality microscopes is very nearly the same for all manufacturers.

Iris type diaphragms cannot be used since diaphragms are not available for the small apertures typical of microscope objectives. Even if they were available, it would be very difficult to mount them properly at the aperture stop of the microscope objective.

However, if the source is imaged in the objective, the principal requirement of a condenser system will be fulfilled. That is, every point of the source will be illuminating any point in the object being examined. This type of illumination is used in projection systems and has not been seen to produce the "ringing" which is characteristic of coherent illumination systems.

Therefore, one objective of this invention is to provide a microdensitometer which is capable of submicron resolution. Another objective of this invention is to provide a simple apparatus for adjusting the coherence of the illumination in a microdensitometer.

SUMMARY OF THE INVENTION

A microdensitometer capable of submicron resolution is achieved by employing large numerical aperture input and output microscopes in conjunction with an external diaphragm placed behind the output microscope. This arrangement allows the ready adjustment of both the position and size of the diaphragm thereby retaining a high degree of incoherence in the output and achieving submicron resolution.

LIST OF REFERENCE NUMERALS

FIG. 1

Figure 1:
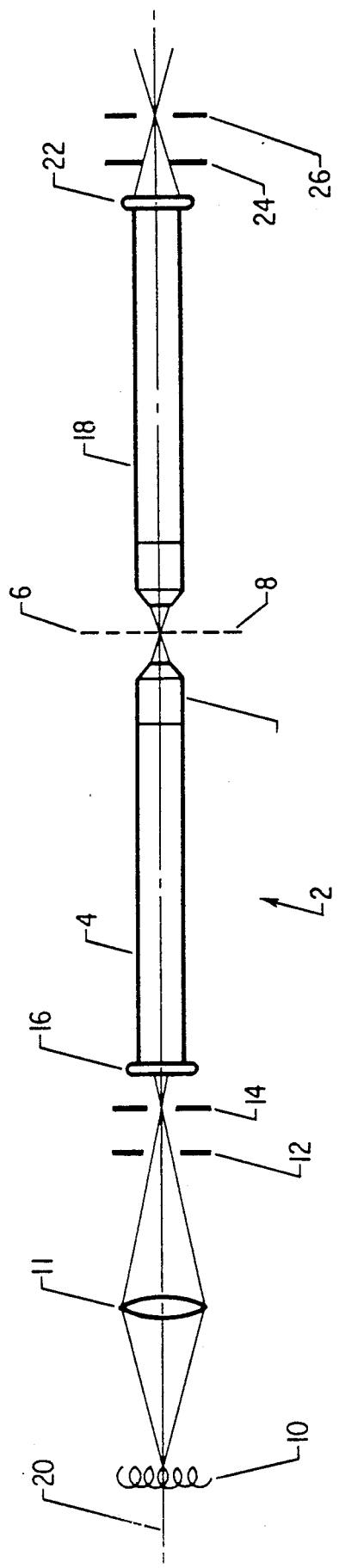
FIG. 1 is a schematic illustration of a microdensitometer according to the present invention.

2: microdensitometer
4: input microscope
6: film sample
8: focal plane
10: light source
11: condenser
12: input slit
14: diaphragm
16: input eyepiece
18: output microscope
20: optical axis
22: output eyepiece
24: adjustable diaphragm
26: output slit

FIG. 2

A. $NA_c/NA_o = 1.0$
B. $NA_c/NA_o = 0.8$

DETAILED DESCRIPTION OF THE PREFERRED EMBODIMENT

Referring to FIG. 1, a microdensitometer 2 of the present invention is illustrated. Microdensitometer 2 includes an input microscope 4 which illuminates film sample 6 located at focal plane 8. Illumination is provided by light source 10 which is focused by condenser 11 through input slit 12. Stray light is blocked by diaphragm 14 before the illumination from source 10 enters input eyepiece 16 of input microscope 4. An output microscope 18 is placed along optical axis 20 to collect light from the image formed on film sample 6 located at focal plane 8. That image light passes through output eyepiece 22, adjustable diaphragm 24 and output slit 26.

Adjustable diaphragm 24 is disposed along optical axis 20 behind the output eyepiece 22. Diaphragm 24 is mounted to permit the position and size of diaphragm 24 to be readily adjusted.

The image formed by the diaphragm is situated roughly one eyepiece focal length behind (outside) the output eyepiece 22. That area is very accessible compared to the constricted area around the rear surface of the microscope objective. The diaphragm 24 when placed in accordance with the present invention affects the system exactly as would one situated in the objective.

Small longitudinal motions of the diaphragm 24 will cause it to be projected into any position internal to the objective should it turn out that better performance can be realized by placing the diaphragm image internally to the objective understandable to those skilled in the art. This is very difficult to do by placing diaphragms in the objective.

This arrangement permits the ready adjustment of the position and size of the diaphragm, the elimination of the coherence effects (ringing) for a minimum loss of resolution, and the attainment of optimum performance.

Diaphragm 14 can be used for a different purpose on the input microscope 4. Diaphragm 14 was placed at the image of the objective formed by the input eyepiece 16. In this instance, the diaphragm 14 was made slightly larger than the entrance pupil of the input microscope objective. Condenser 11 was caused to form an image of the source on diaphragm 14 and the eyepiece 16 relayed this image so that the image of the diaphragm 14 formed by the eyepiece 16 is in focus on the objective. Image 16 is in focus on the objective. Thus the source was imaged into the objective in such a way that no light strikes the inside of the barrel of the input microscope 4, thereby eliminating the primary cause of stray light. No tube diaphragming is necessary.

Figure 2:
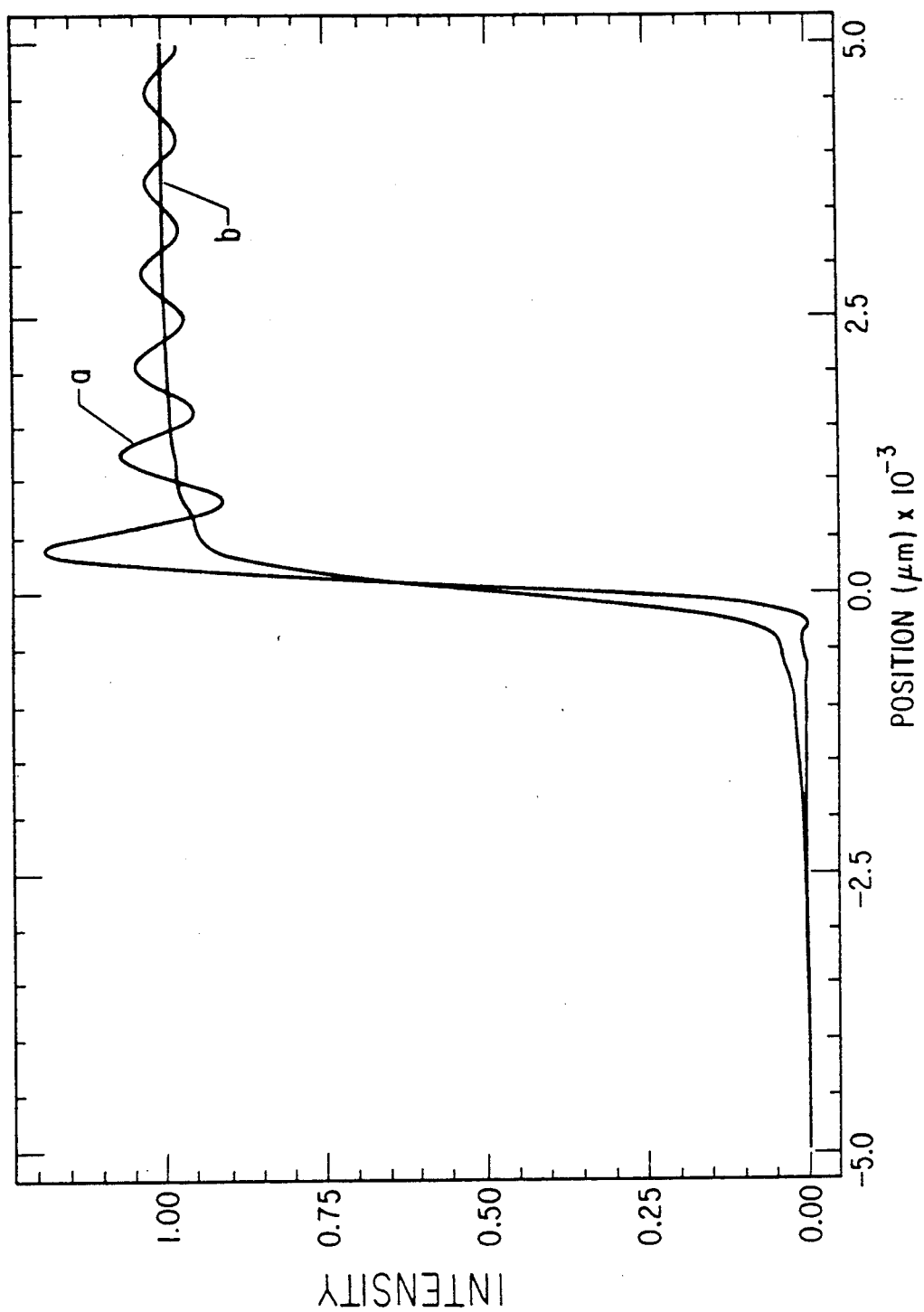
FIG. 2 is a knife edge trace showing the total absence of coherence in the present system.

FIG. 2 is a microdensitometer knife edge trace which demonstrates an experimental verification of the optical performance of the subject invention. FIG. 2 plots intensity against position ($\mu M$). FIG. 2 shows how the transmitted intensity appears to vary for coherent and non-coherent illumination. The ratio of NAc/NAo is about 0.8 for curve "B" and 1.0 for curve "A".

Figure 3:
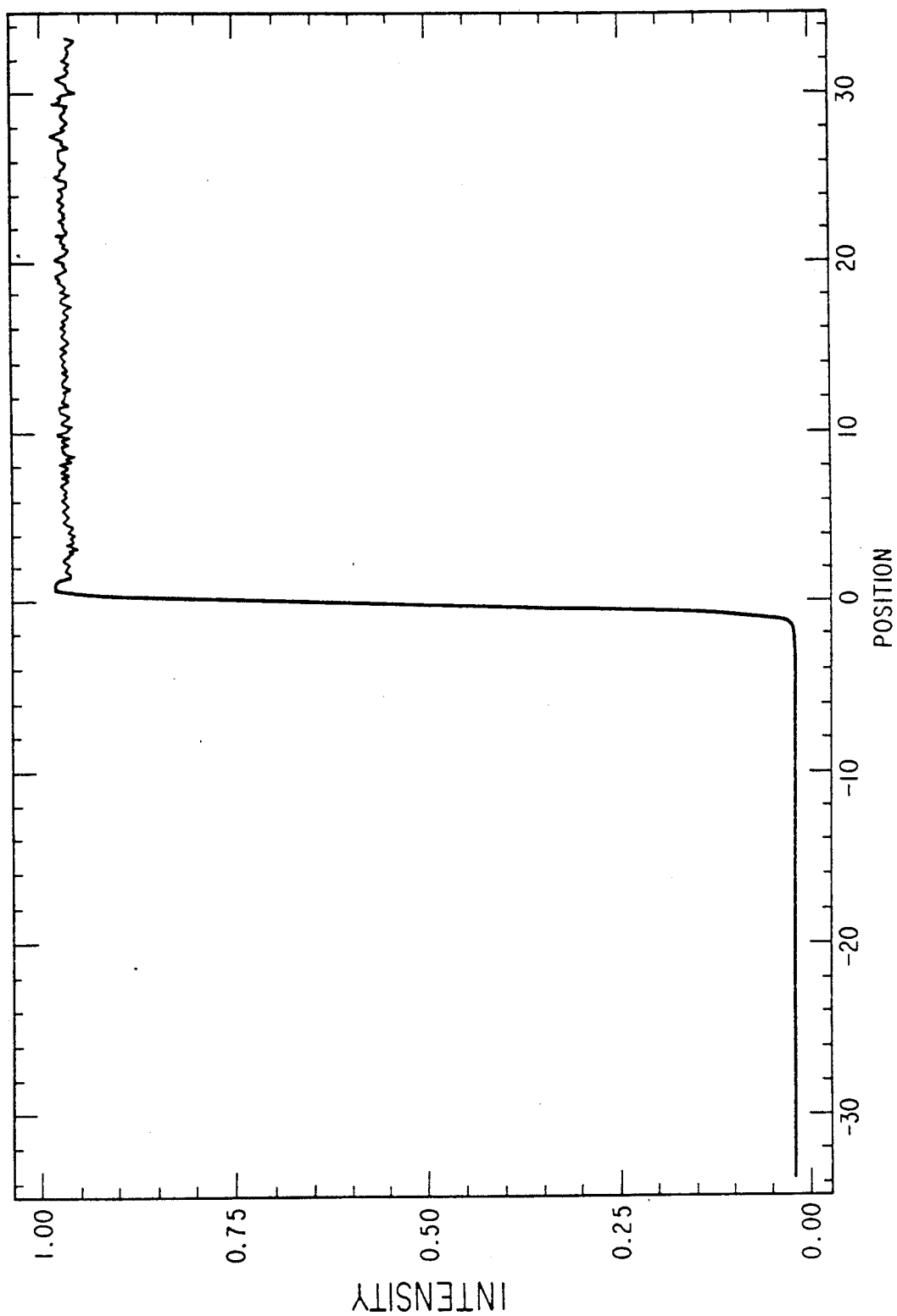
FIG. 3 is a knife edge trace of a non-coherent system.

FIG. 3 is a knife edge trace on a larger scale of the performance of the present invention This trace closely approximates the curve in FIG. 2 for a non-coherent optical system.

The foregoing description of an embodiment of this invention is given by way of illustration and not limitation. As will be readily apparent to one skilled in the art, many modifications can be made to this invention without departing from the scope of the invention.

I claim:

1. A microdensitometer capable of submicron resolution, comprising:
   a. a light source;
   b. a condenser lens;
   c. an input diaphragm for adjusting an input microscope, disposed on an axis formed by the light source and the condenser lens;
   d. said input microscope with a predetermined focal plane, disposed on the axis formed by the light source, the condenser lens, and the input diaphragm;
   e. an output microscope having a clear aperture and an objective, disposed on the same axis as the input microscope, having the same focal plane as the input microscope;
   f. a sample disposed on said focal plane;
   g. an output diaphragm for adjusting the clear aperture of the output objective to achieve non-coherent illumination;
   h. whereby an image of the sample is illuminated by light traveling through the input microscope and is examined by the output microscope.

* * * * *